(12) United States Patent
Shioda

(10) Patent No.: US 9,730,869 B2
(45) Date of Patent: Aug. 15, 2017

(54) HAIR COLORING AGENT AND HAIR DYEING METHOD

(71) Applicant: ICTB GLOBAL CO., LTD., Yokohama-shi, Kanagawa (JP)

(72) Inventor: Masataka Shioda, Yokohama (JP)

(73) Assignee: ICTB GLOBAL CO., LTD., Yokohama (JP)

( * ) Notice: Subject to any disclaimer, the term of this patent is extended or adjusted under 35 U.S.C. 154(b) by 0 days.

(21) Appl. No.: 14/900,870

(22) PCT Filed: Sep. 11, 2014

(86) PCT No.: PCT/JP2014/004695
§ 371 (c)(1),
(2) Date: Dec. 22, 2015

(87) PCT Pub. No.: WO2016/038646
PCT Pub. Date: Mar. 17, 2016

(65) Prior Publication Data
US 2016/0199270 A1    Jul. 14, 2016

(51) Int. Cl.
*A61Q 5/10* (2006.01)
*A61K 8/19* (2006.01)
*A61K 8/97* (2017.01)
*A61K 8/22* (2006.01)
*A61K 8/34* (2006.01)

(52) U.S. Cl.
CPC ............... *A61K 8/19* (2013.01); *A61K 8/22* (2013.01); *A61K 8/342* (2013.01); *A61K 8/97* (2013.01); *A61Q 5/10* (2013.01); *A61K 2800/413* (2013.01); *A61K 2800/4324* (2013.01); *A61K 2800/81* (2013.01); *A61K 2800/884* (2013.01)

(58) Field of Classification Search
CPC ... A61Q 5/10; A61Q 5/06; A61K 8/22; A61K 8/97; A61K 8/19; A61K 2800/4324; A61K 2800/884
See application file for complete search history.

(56) References Cited

U.S. PATENT DOCUMENTS

| | | | |
|---|---|---|---|
| 2006/0248663 A1 | 11/2006 | Tremblay et al. | |
| 2010/0251488 A1 | 10/2010 | Fujinuma et al. | |
| 2013/0206159 A1* | 8/2013 | Kodama | A61K 8/22 132/208 |

FOREIGN PATENT DOCUMENTS

| | | | |
|---|---|---|---|
| CN | 101166560 A | 4/2008 | |
| CN | 102716042 A | 10/2012 | |
| JP | 2004-224792 A | 8/2004 | |
| JP | 2005-213212 A | 8/2005 | |
| JP | 2012-056923 A | 3/2012 | |
| JP | 2012-071114 A | 4/2012 | |
| JP | 4993396 * | 8/2012 | ............... A61Q 5/10 |
| JP | 4993396 B1 | 8/2012 | |
| JP | 2013-067597 A | 4/2013 | |
| JP | 5606590 B1 | 10/2014 | |

OTHER PUBLICATIONS

English translation of the Japanese reference No. 2012-056923 (Mar. 22, 2012).*
English translation (Mar. 10, 2017) of the Korean reference No. 10-2013-0033291.*
Dec. 9, 2014 International Search Report issued in International Patent Application No. PCT/JP2014/004695.
Dec. 9, 2014 Written Opinion issued in International Patent Application No. PCT/JP2014/004695.
Oct. 11, 2016 Office Action issued in Korean Patent Application No. 10-2015-7036416.

* cited by examiner

*Primary Examiner* — Eisa Elhilo
(74) *Attorney, Agent, or Firm* — Oliff PLC

(57) ABSTRACT

Disclosed is a two-agent type hair coloring agent prepared by mixing a first agent and a second agent, wherein the first agent contains a dye component containing a basic dye as a main component, and an alkaline agent, the second agent contains a hydrogen peroxide solution as a main component thereof, and at least one of the first agent and the second agent further contains metal nanoparticles.

9 Claims, No Drawings

HAIR COLORING AGENT AND HAIR DYEING METHOD

TECHNICAL FIELD

The present invention relates to a hair coloring agent that can be preferably used for the so-called cosmetic hair dyeing for dyeing mainly black hair to a bright color. More particularly, the invention relates to a hair coloring agent capable of achieving cosmetic hair dyeing without using an oxidation dye, and retaining the color for a long period of time.

BACKGROUND ART

Conventionally, oxidation hair dyeing agents containing a p-phenylenediamine-type oxidation dye or an aminophenol-type oxidation dye, which are synthetic dyes, are widely used. Usually, the oxidation hair dyeing agent is a two-agent type hair coloring agent prepared by mixing a first agent and a second agent, wherein the first agent contains an oxidation dye and an alkaline agent, and the second agent contains a hydrogen peroxide solution as a main component. The Hydrogen peroxide solution has the functions of serving as an oxidizing agent for oxidatively polymerizing the oxidation dye to develop its color and a bleaching agent for decomposing the melanin pigment in the hair.

In use of such an oxidation hair dyeing agent, the first agent and the second agent are mixed immediately before application, and the mixture is applied onto the hair. When the oxidation hair dyeing agent is applied, the oxidation dye penetrated into the hair is oxidatively polymerized in the hair thereby to generate a bulky indo-dye, and the indo-dye develops its color. The indo-dye is not easily removed from the hair because of its bulkiness, making it possible to provide excellent color retention of the dyed hair and achieve a wide variety of color tones.

However, it is known that oxidation dyes may cause skin disorders. Furthermore, it has been pointed out that oxidation dyes are endocrine disruptors that adversely affect an ecosystem, and also that they allegedly produce cancers, allergies, and the like. For this reason, the use of oxidation hair dyeing agents is restricted in Europe and other countries.

Basic dyes are known as dyes that are safer than oxidation dyes. A basic dye is deposited as a result of its cation being ionically bonded to the anion of the keratin protein on the surface of the hair. Conventionally, the basic dye has been used, for example, as a hair manicure that lasts only about one to two weeks, as well as a color rinse and a color treatment that continue to provide color by being used several times a week.

For example, Patent Literature 1 below discloses, as a hair dyeing and hairdressing composition that achieves both a hairdressing effect and a hair dyeing effect, a hair dyeing and hairdressing composition containing a hair dyeing pigment that is at least one dye or pigment selected from an HC dye, a basic dye, a disperse dye and a natural pigment, as well as at least one α-hydroxy acid ester and/or at least one dialkyl carbonate, and at least one cross-linked polymer. Such a composition is a color treatment agent that fixes the dye by forming a polymer coating on the surface of the hair, and gradually colors the hair through frequent use. Accordingly, the composition disclosed in Patent Literature 1 is not used for cosmetic hair dyeing for dyeing black hair to a bright color, and cannot achieve long-term color retention by a single application.

Patent Literature 2 below, which discloses an invention made by the present inventors, discloses a hair dyeing method including a first step of applying, to hair, a base color dye liquid containing a basic dye and an HC dye serving as a main dye component and leaving the hair for a predetermined period of time, a second step of rinsing the hair on which the base color dye liquid has been applied, and a third step of, after the second step, applying an aqueous solution of tea catechin onto the hair and leaving the hair for a predetermined period of time. However, this technique is mainly used to fix the dye onto the hair that has been subjected to gray hair dyeing, and such a technique cannot be used for cosmetic hair dyeing for dyeing black hair to a bright color.

CITATION LIST

[Patent Literatures]
[Patent Literature 1] Japanese Laid-Open Patent Publication No. 2005-213212
[Patent Literature 2] Japanese Patent No. 4993396

SUMMARY OF INVENTION

Technical Problem

Basic dyes are considered to be safer than oxidation dyes. However, basic dyes are disadvantageous in that they penetrate poorly into the deep portion of the hair due to their higher molecular weight, and that they are deposited onto the keratin protein by ionic bonding with a weak bonding force, resulting in poor color retention of the dyed hair. Therefore, basic dyes have not been applied to a use intended to achieve color retention for a period exceeding a month, such as the use as the so-called permanent hair dyeing agent.

It is an object of the present invention to provide a two-agent type hair coloring agent with which it is possible to achieve cosmetic hair dyeing that provides long-term color retention, even in the case of using a basic dye as a base color.

Solution to Problem

A hair coloring agent according to the present invention is a two-agent type hair coloring agent prepared by mixing a first agent and a second agent, wherein the first agent contains a dye component containing a basic dye as a main component, and an alkaline agent, the second agent contains a hydrogen peroxide solution as a main component thereof, and at least one of the first agent and the second agent further contains metal nanoparticles.

Such a hair coloring agent can improve the color retention of the dye without containing an oxidation dye, even in the case of performing cosmetic hair dyeing for dyeing black hair in a bright color, or more specifically, in the case of performing hair dyeing by causing a basic dye to penetrate into the hair while appropriately bleaching the melanin pigment in the hair with hydrogen peroxide.

Although the mechanism behind the improved color retention of the basic dye has not been clarified at this moment, it seems that due to the action of the electric charge on the surface of colloidal particles in the aqueous solution containing hydrogen peroxide, metal nanoparticles such as gold nanoparticles or platinum nanoparticles promoted penetration of the basic dye into the hair and further promoted generation of the cation of the basic dye, thereby facilitating ionic bonding of the cation of the basic dye to the anion of the keratin protein. That is, it is believed that blending the metal nanoparticles results in activation of the cation of the basic dye and the cation has become more easily adsorbed onto the anion of the keratin of the hair, thereby improving the hair dyeing property. As a result, it seems that, for example, about 5 to 30% of all pigments including the melanin pigment was successfully replaced by the dye in the hair. With a hair coloring agent according to the present invention, it is possible to achieve cosmetic hair dyeing that provides colors without lowering brightness excessively, such as Levels 8 to 10 defined on Hair Coloring Level Scale sold by JAPAN HAIR COLOR ASSOCIATION (JHCA).

It is preferable that the hair coloring agent contains the hydrogen peroxide solution in an amount corresponding to a proportion such that 30 to 70 mass % of a 4.5 mass % hydrogen peroxide solution is blended, since the hair coloring agent can be particularly preferably used for cosmetic hair dyeing for dyeing dark hair in a bright color while increasing the brightness of the hair by causing the basic dye to penetrate into the hair while adequately decomposing the melanin pigment in the hair with hydrogen peroxide.

It is also preferable that the dye component further contains an HC dye since this increases the degree of freedom of toning. At this time, when the total content of the basic dye and the HC dye in the prepared hair coloring agent is 0.1 to 10 mass %, it is possible to achieve cosmetic hair dyeing without lowering brightness excessively.

A hair dyeing method according to the present invention is a hair dyeing method including: a first step of applying any of the above-described hair coloring agents onto hair and leaving the hair for a predetermined time; a second step of rinsing the hair on which the hair coloring agent is applied; and a third step of, after the second step, applying an aqueous solution of tea powder onto the hair and leaving the hair for a predetermined period of time. With such a method, it is possible to further suppress the color loss in hair described above.

[Advantageous Effects of Invention]

The hair coloring agent according to the present invention makes it possible to perform hair dyeing that achieves color retention for a long period of time by using a basic dye as a base color, without containing any oxidation dye. In particular, the hair coloring agent of the present invention makes it possible to perform the so-called cosmetic hair dyeing for dyeing dark hair in a bright color by causing the basic dye to penetrate into the hair, while increasing the brightness of the hair by bleaching the hair by appropriately decomposing the melanin pigment in the hair with the hydrogen peroxide in the hydrogen peroxide solution.

DESCRIPTION OF EMBODIMENT

Hereinafter, an embodiment of the hair coloring agent according to the present invention will be described in detail.

The hair coloring agent of the present invention is a two-agent type hair coloring agent prepared by mixing a first agent and a second agent, wherein the first agent contains a dye component containing a basic dye as a main component, and an alkaline agent, the second agent contains a hydrogen peroxide solution as a main component, at least one of the first agent and the second agent further contains metal nanoparticles such as gold nanoparticles or platinum nanoparticles, and the hair coloring agent preferably contains no oxidation dye.

The first agent is an agent containing a dye component containing a basic dye as the main component and an alkaline agent serving as a pH regulator, and optionally, a cream base, a conditioning agent, a stabilizer, a perfume, a solvent, and the like. In order to maintain the activity of the alkaline agent, it is preferable that the agent containing an alkaline agent and the agent containing a dye component are mixed immediately before use to prepare the first agent.

The dye component contains a basic dye as a main component. The proportion of the basic dye in the dye component is preferably 50 mass % or more, more preferably 60 mass % or more, particularly preferably 80 mass % or more. By using the basic dye as the main component of the dye component in this manner, it is possible to achieve highly safe hair coloring.

The basic dye is a dye that has an amino group, a substituted amino group, or the like in the molecule and becomes a cation in an aqueous solution. Those conventionally known as basic dyes may be used without any particular limitation. Because the basic dye becomes a cation in an aqueous solution, it is deposited by being ionically bonded to the anion of the keratin protein on the surface of the hair. Specific examples thereof include Basic Blue 7 (C.I.42595), Basic Blue 16 (C.I.12210), Basic Blue 22 (C.I.61512), Basic Blue 26 (C.I.44045), Basic Blue 99 (C.I.56059), Basic Blue 117, Basic Violet 10 (C.I.45170), Basic Violet 14 (C.I.42515), Basic Brown 16 (C.I.12250), Basic Brown 17 (C.I.12251), Basic Red 2 (C.I.50240), Basic Red 12 (C.I.48070), Basic Red 22 (C.I.11055), Basic Red 51, Basic Red 76 (C.I.12245), Basic Red 118 (C.I.12251:1), Basic Orange 31, Basic Yellow 28 (C.I.48054), Basic Yellow 57 (C.I.12719), Basic Yellow 87, and Basic Black 2 (C.I.11825). These may be used alone or in a combination of two or more.

Specific examples of the dyes other than the basic dye that can be used as the dye component include an HC dye and a polyphenol dye. From the viewpoint of safety, it is preferable that no oxidation dye is contained.

An HC dye is a dye with the known prefix "HC" and has a small molecular size. Accordingly, it penetrates into the hair to be deposited therein by hydrogen bonding and intermolecular attraction, providing a deeper color development. Specific examples thereof include HC Blue No. 2, HC Blue No. 8, HC Orange No. 1, HC Orange No. 2, HC Red No. 1, HC Red No. 3, HC Red No. 7, HC Red No. 8, HC Red No. 10, HC Red No. 11, HC Red No. 13, HC Red No. 16, HC Violet No. 2, HC Yellow No. 2, HC Yellow No. 5, HC Yellow No. 6, HC Yellow No. 7, HC Yellow No. 9, and HC Yellow No. 12. These may be used alone or in a combination of two or more.

An alkaline agent is a component that promotes penetration of effective components such as dye components and hydrogen peroxide by opening the cuticle by swelling the hair, and promotes decomposition of the melanin pigment by enhancing the oxidation capability of hydrogen peroxide. Specific examples of the alkaline agent include ammonia water, ammonium carbonate, sodium carbonate, monoethanolamine, ammonium hydrogencarbonate, and arginine. Among these, ammonia water and ammonia hydrogen carbonate water are particularly preferable. These may be used alone or in a combination of two or more. The pH of the first agent containing an alkaline agent is, but not particularly limited to, preferably 9 or more, more preferably 10 or more.

A cream base is a component that emulsifies the first agent into a cream form, thereby improving the handleability. As specific examples of the cream base, known cream bases obtained by appropriately blending an oil component such as cetanol, stearyl alcohol, octyldodecanol, oleyl alcohol, isostearyl alcohol, mineral oil, decyl oleate, isostearyl myristate, isopropyl palmitate or triglycery and an emulsifier such as polyoxyethylene lauryl ether, sorbitan laurate, Ceteth-2, Oleth-10 or Cetoleth-20 can be used without any particular limitation.

As the conditioning agent, various nutrients for moisturizing hair, various humectants, and the like are optionally blended. Specific examples thereof include nutrients such as a keratin, cysteine, and plant extracts such as a garlic extract, a rosemary extract and a pine extract; humectants such as polyethylene glycol. As the stabilizer, an antioxidant for preventing deterioration of the dye, a chelating agent such as EDTA, and the like are optionally blended. As the perfume, known perfumes for alleviating, for example, an irritating odor of the alkaline agent such as ammonia are optionally blended. Additionally, as the solvent, purified water and various organic solvents are optionally blended.

The first agent is prepared preferably in the form of a cream or a paste by blending the agent serving as the base color containing the basic dye and the optionally blended HC dye and the like and the agent containing an alkaline agent, as described above, at a predetermined ratio.

The concentration of the dye component contained in the first agent is, but not particularly limited to, preferably 1 to 10 mass %, more preferably 0.5 to 5 mass %, for example.

Meanwhile, the second agent is a component containing a hydrogen peroxide solution as a main component, and this component is also called "oxidation agent" in the case of hair coloring using an oxidation dye. The Hydrogen peroxide solution has the function of serving as the bleaching agent for decomposing the melanin pigment in the hair to achieve enhanced brightness.

In the hair coloring agent of the present invention, at least one of the first agent and the second agent, preferably the first agent, contains metal nanoparticles such as gold nanoparticles or platinum nanoparticles. By blending the metal nanoparticles, the basic dye is adsorbed onto the surface of the metal nanoparticles, then directly penetrates into the hair, and is more easily adsorbed onto keratin. Accordingly, it is possible to perform hair dyeing that achieves long-term color retention even in the case of using the basic dye as the base color.

Here, the metal nanoparticles refer to metal nanoparticles capable of forming a colloidal solution and having a particle size of several tens of nanometers, and examples thereof include gold nanoparticles, platinum nanoparticles, silver nanoparticles, and copper nanoparticles. Although the particle size of the metal nanoparticles is not particularly limited as long as the metal nanoparticles are dispersed in a colloidal solution, it is particularly preferable to use gold nanoparticles or platinum nanoparticles having a particle size of, preferably about 10 to 100 nm, more preferably about 10 to 50 nm, in terms of ready availability. A colloidal solution of such metal nanoparticles is commercially available, for example, from Johzen Co. Ltd.

The first agent and the second agent are blended at a predetermined ratio and mixed, to prepare a creamy hair coloring agent, for example. Regarding the blending ratio of the first agent and the second agent, it is preferable, in view of ease of blending, that the second agent is blended preferably 0.6 to 1.5 times the amount of the first agent, more preferably 0.8 to 1.3 times, most preferably approximately 1 time, in terms of mass ratio. Although the pH of the hair coloring agent thus prepared is not particularly limited as long as it is within the range of weakly acidic to weakly alkaline pHs, specifically, the pH is preferably about 4 to 8, more preferably about 4 to 6.

Although the amount of the hydrogen peroxide solution contained in the prepared hair coloring agent is not particularly limited, it is preferable to blend the hydrogen peroxide solution in an amount corresponding to a proportion such that 30 to 70 mass % of a 4.5 mass % hydrogen peroxide solution is blended, for example. When the hydrogen peroxide solution is blended in such a range, about 5 to 30% of all pigments including the melanin pigment in the hair is more easily replaced by the dye, thereby making it possible to achieve cosmetic hair dyeing that provides colors without lowering brightness excessively, such as Levels 8 to 10 defined on Hair Coloring Level Scale sold by JAPAN HAIR COLOR ASSOCIATION (JHCA).

Although the amount of the metal nanoparticles blended in the prepared hair coloring agent is not particularly limited, it is preferable the metal nanoparticles are blended in an amount of preferably 0.0001 to 0.01 mass %, more preferably 0.001 to 0.01 mass %, for example. When the proportion of the metal nanoparticles is too high, the utility is lost because the cost increases too much. When the proportion of the metal nanoparticles is too low, the effect of enhancing adsorption tends to be insufficient.

A method for dyeing hair by using the thus prepared hair coloring agent will be described below.

The hair coloring agent of the present invention is first uniformly applied onto a portion of hair that is to be dyed. Then, the hair on which the hair coloring agent has been applied is left for a predetermined period of time. Although the duration for which the hair is left is appropriately adjusted according to the intended color to be provided to the hair, usually, it is preferably 5 to 60 minutes, more preferably 10 to 30 minutes, from the viewpoint of the operation process. During the period in which the hair is left, it is preferable that the hair on which the hair coloring agent has been applied is uniformly irradiated with far-infrared radiation. Irradiation of the hair with far-infrared radiation can shorten the duration for which the hair is left. The surface temperature of the hair during irradiation with far-infrared radiation is preferably 20 to 40° C., more preferably about 25 to 35° C., from the viewpoint of preventing the hair from being damaged and an excessive burden on the human body.

Then, the hair on which the hair coloring agent has been applied is rinsed. Although the method of rinsing is not particularly limited as long as the hair coloring agent attached onto the hair can be washed off, it is preferable that the hair coloring agent is washed off with water or lukewarm water, preferably with the use of a shampoo. After washing, towel drying is usually performed.

The hair coloring agent of the present invention is preferably used for the so-called cosmetic hair dyeing for dyeing dark hair in a bright color, while increasing the brightness of the hair by decomposing the melanin pigment in the hair with hydrogen peroxide, and gray hair dyeing for dyeing gray hair. It is particularly preferable to use the hair coloring agent for cosmetic hair dyeing. With the use of the hair coloring agent of the present invention, it is possible to achieve cosmetic hair dyeing that prevents color loss for a long period of time without using an oxidation dye and that provides colors without lowering brightness excessively, such as Levels 8 to 10 defined on Hair Coloring Level Scale sold by JAPAN HAIR COLOR ASSOCIATION (JHCA).

The hair coloring agent of the present invention can also be used for gray hair dyeing. Particularly, in the case of gray hair dyeing, it is preferable to perform, after dyeing, the following hair treatment in order to further prevent color loss.

A hair treatment is a step of applying an aqueous solution (aqueous dispersion) of tea powder onto the rinsed hair, and leaving the hair for a predetermined period of time. The aqueous solution of tea powder is, for example, a paste-like aqueous solution containing tea powder as a main component.

Tea powder is a powder obtained by pulverizing tea leaves, and examples thereof include a fresh tea powder, a steamed tea powder, and a Japanese Matcha tea powder. Although most tea leaves may be often steamed or roasted in order to suppress fermentation, the tea powder in the present invention is preferably a powder that has not been subjected to such a treatment and contains tea catechin derived from fresh tea, such as epigallocatechin gallate, at a high concentration because it can retain the color for a longer period of time.

The aqueous solution of tea powder can be prepared in a paste form, for example, by dissolving or dispersing tea powder in water. Although the content of the tea powder dissolved in the aqueous solution of tea powder is not particularly limited, specifically, it is preferably 5 mass % or more, more preferably 10 mass % or more, particularly preferably 15 mass % or more.

By applying the aqueous solution of tea powder onto the hair and leaving the hair for a predetermined period of time, the dye that has penetrated into or has been deposited on the hair is more firmly fixed onto the hair. Although the mechanism of this function has not been fully determined, it is believed, based on many test results, that highly active tea catechin is oxidatively polymerized by oxygen in the air to form, for example, a coating that covers the basic dye and the like fixed to the anionic group of the keratin protein, and this coating suppresses color loss over time. Such a mechanism is presumed also based on the fact that the effect is increased by irradiation with far-infrared radiation during the period in which the hair is left. That is, color loss over time can be further suppressed by irradiating the hair with far-infrared radiation after application of the aqueous solution of tea powder.

Regarding the conditions for the irradiation with far-infrared radiation, the surface temperature of the hair is preferably 20 to 40° C., more preferably about 25 to 35° C., and the irradiation time is preferably 10 to 60 minutes, more preferably, 15 to 30 minutes, from the viewpoint of excellent operation efficiency and preventing the hair from being damaged and an excessive on the human body. Color loss can be further suppressed by leaving the hair for a predetermined period of time after the irradiation with far-infrared radiation.

Then, the hair on which the aqueous solution of tea powder has been applied and left for a predetermined period of time, preferably after being irradiated with far-infrared radiation, is subjected to finishing shampooing to wash off the aqueous solution of tea powder. After washing, towel drying, air drying, and the like are performed. By performing such a hair treatment, it is possible to further suppress color loss of the hair dyed with the hair coloring agent of the present invention.

EXAMPLES

Hereinafter, the present invention will be described in further detail by way of examples. It should be appreciated that the scope of the present invention is by no means limited by the examples.

Example 1

A gold nanocolloid (manufactured by Johzen Co. Ltd.) was added dropwise to 50 g of a base color dye obtained by mixing a cream base composed mainly of cetanol with 5 mass % of a dye mixture obtained by mixing a basic dye and an HC dye serving as dye components at 9:1, and 50 g of alkaline agent containing ammonia water and ammonium hydrogencarbonate was further mixed therewith, to prepare a first agent. The gold nanocolloid was prepared such that 0.0005 mass % of the gold nanoparticles was contained in the first agent.

Then, 30 g of a 4.5% hydrogen peroxide solution was mixed with 30 g of the first agent, to prepare a hair coloring agent.

Next, the prepared hair coloring agent was applied onto the hair of a female subject who had black hair and almost no gray hair. Then, the hair on which the hair coloring agent had been applied was left for 10 minutes, and thereafter was irradiated with far-infrared radiation for about 15 minutes. At this time, the temperature of the hair was about 30° C.

Then, the hair was washed with a commercially available shampoo. Then, the water on the hair was fully wiped off with a towel. In this way, the hair was subjected to cosmetic hair dyeing. At this time, it was confirmed that the hair was uniformly dyed in Level 8 brown color.

Then, the dyed hair was shampooed once a day, and the change in the color of the hair was observed. As a result, the hair was still uniformly dyed in Level 8 brown color after an elapse of one month.

Example 2

Hair dyeing was performed in the same manner as in Example 1 except that a platinum nanocolloid (manufactured by Johzen Co. Ltd.) was used in place of the gold nanocolloid used in Example 1, and evaluation was made. As a result, the hair was still uniformly dyed in Level 8 brown color after an elapse of one month.

Example 3

Hair dyeing was performed in the same manner as in Example 1 except that the hair of a female subject with a lot of gray hair, in place of the female subject with black hair, was dyed, and evaluation was made. As a result, the brown dye at the dyed portion mostly remained after an elapse of one month, but the hair became somewhat grayish.

Example 4

Hair dyeing was performed in the same manner as in Example 1 except that the hair of a female subject with a lot of gray hair, in place of the female subject with black hair, was dyed.

Next, 25 g of tea powder (manufactured by ICTB global., Ltd.; tea color treatment powder, powder of fresh Japanese Uji tea) was dissolved in 175 g of lukewarm water, to prepare an aqueous solution of tea powder. Then, the prepared aqueous solution of tea powder was applied onto the hair. Then, the hair on which the aqueous solution of tea powder had been applied was left for 10 minutes, and thereafter irradiated with far-infrared radiation for about 20 minutes. At this time, the temperature of the hair was about 30° C. Then, the hair was further left for about 10 minutes.

Then, the hair was washed with a commercially available shampoo. Then, the water on the hair was fully wiped off with a towel. As a result, after an elapse of one month, a clearly more amount of the brown dye at the dyed portion remained as compared with Example 3, and the gray hair became inconspicuous.

Comparative Example 1

Hair dyeing was performed in the same manner as in Example 1 except that the gold nanocolloid was not added dropwise, and evaluation was made. As a result, after an elapse of one month, the color of the hair was too much brighter than the colors in Examples 1 and 2. This result showed that the adsorption of the basic dye was lower when the metal nanocolloid as used in Example 1 or 2 was not added dropwise.

INDUSTRIAL APPLICABILITY

When hair dyeing is performed by using the hair coloring agent according to the present invention, it is possible to retain the color for a long period of time even in the case of using a basic dye as a base color. Accordingly, using a basic dye as a base color, the hair coloring agent of the present invention can be used as an alternative to the so-called permanent hair dye that enables long-term color retention, not for dyeing such as color treatment intended for short-term color retention. The hair coloring agent according to the present invention can be particularly preferably used for cosmetic hair dyeing.

The invention claimed is:

1. A two-agent type hair coloring agent prepared by mixing a first agent and a second agent,
   wherein the first agent contains a dye component containing a basic dye as a main component, and an alkaline agent,
   the second agent contains a hydrogen peroxide solution as a main component thereof, and
   at least one of the first agent and the second agent further contains metal nanoparticles, wherein the metal nanoparticles are gold nanoparticles or platinum nanoparticles.

2. The hair coloring agent according to claim 1, wherein the hair coloring agent contains no oxidation dye.

3. The hair coloring agent according to claim 1, wherein the hair coloring agent contains the hydrogen peroxide solution at a concentration of 4.5 mass % in an amount corresponding to a proportion such that 30 to 70 mass % of the hydrogen peroxide solution is blended, relative to 100 mass % of the second agent.

4. The hair coloring agent according to claim 1, wherein the dye component further contains an HC dye.

5. A hair dyeing method comprising:
   a first step of applying a two-agent type hair coloring agent onto hair and leaving the hair for a predetermined time;
   a second step of rinsing the hair on which the hair coloring agent is applied;
   wherein the two-agent type hair coloring agent is prepared by mixing a first agent and a second agent, the first agent containing a dye component containing a basic dye as a main component, and an alkaline agent, and the second agent containing a hydrogen peroxide solution as a main component thereof, and at least one of the first agent and the second agent further contains metal nanoparticles wherein the metal nanoparticles are gold nanoparticles or platinum nanoparticles.

6. The hair dyeing method according to claim 5, wherein the hair coloring agent contain no oxidation dye.

7. The hair dyeing method according to claim 5, wherein the hair coloring agent contains the hydrogen peroxide solution at a concentration of 4.5 mass % in an amount corresponding to a proportion such that 30 to 70 mass % of the hydrogen peroxide solution is blended, relative to 100 mass % of the second agent.

8. The hair dyeing method according to claim 5, wherein the dye component further contains an HC dye.

9. The hair dyeing method according to claim 5, further comprising
   a third step of, after the second step, applying an aqueous solution of tea powder onto the hair and leaving the hair for a predetermined period of time.

* * * * *